United States Patent [19]

Sanders et al.

[11] 4,155,909

[45] May 22, 1979

[54] 2-ALKYL NICOTINOIDS AND PROCESSES FOR THEIR PRODUCTION

[75] Inventors: Edward B. Sanders, Richmond; Henry V. Secor, Midlothian; Jeffrey I. Seeman, Richmond, all of Va.

[73] Assignee: Philip Morris Incorporated, New York, N.Y.

[21] Appl. No.: 805,689

[22] Filed: Jun. 13, 1977

[51] Int. Cl.$^2$ .......................................... C07D 401/02
[52] U.S. Cl. ..................................... 546/193; 424/263; 546/255; 546/257; 546/281; 546/282; 546/194; 546/346; 546/286; 546/246; 546/315; 546/330; 546/258; 546/264; 544/124
[58] Field of Search ............. 260/296 R, 297 R, 294.9

[56] References Cited

PUBLICATIONS

Klingsberg, Pyridine and Its Derivatives, Part Three, frontispage, pp. 76 and 136, Interscience Publishers, (1962).
Beilstein's Handbuch der Organischen Chemie, 4th Ed., vol. 23, Mainwerke, system No. 3470, pp. 116–117, Verlag von Julius Springer, (Berlin), 1936.
Beilstein's Handbuch der Organischen Chemie, 4th Ed., vol. 23, Zweites Erganzungswerk, pp. 107–111, Springer-Verlag, Berlin, Germany, 1954.

*Primary Examiner*—John D. Randolph
*Attorney, Agent, or Firm*—Arthur I. Palmer, Jr.; George E. Inskeep; Susan A. Hutcheson

[57] ABSTRACT

The invention relates to 2-alkyl nicotinoids and improved methods for producing them.

6 Claims, No Drawings

2-ALKYL NICOTINOIDS AND PROCESSES FOR THEIR PRODUCTION

The present invention relates to a group of novel nicotine analogues containing alkyl substituents ortho to the pyrrolidine ring. The synthetic procedures disclosed herein for the production of nicotine analogues constitute considerably shorter and more practical routes than those previously proposed. The novel compounds produced by the methods of the present invention are useful as insecticides.

BACKGROUND OF THE INVENTION

Nicotine has been used as an insecticide for many years (see, for example, D. E. H. Frear, "Chemistry of the Pesticides," 3rd Ed., D. Van Nostrand Co., New York, 1955). Although a number of natural as well as synthetic nicotinoids have been screened with regard to insecticidal activity, the vast majority are significantly less active than nicotine [see I. Yamamoto et al., Agr. biol. Chem. 32, 1341 (1968)]. The analogues of nicotine which have been tested involve either the alteration of the pyrrolidine moiety of the molecule, or the replacement of the pyridine ring with a substituted aromatic ring. Almost no work has been carried out with regard to examining the effects of pyridine substituents on insecticidal activity. F. Haglid et al. Acta. Chem. Scand., 21, 329, (1967) treated 1-nicotine with methyl-lithium to yield at 5:1 mixture of 6-methylnicotine and 4-methylnicotine. The latter isomer was found to possess little or no nicotinic activity while 6-methylnicotine was identical in pharmacological activity to nicotine itself. This result indicates that the effect of a methyl group substituent ortho- to the pyrrolidine ring on the pyridine ring plays a major role in nicotinic activity in mammals; however the effect of such a methyl substituent on insecticidal activity has not been previously determined. The ultimate ability of an insecticide depends not only on its absolute insecticidal activity but also on its specificity; i.e., a compound with moderate insecticidal activity which is nontoxic to mammals would be desirable. As a consequence, the synthesis of ortho-alkylated nicotinoids and their evaluation as insecticides is of considerable interest. Haglid was unable to isolate 2-methylnicotine using the method referred to above; however, he presented evidence that indicates that a trace amount may have been present in the reaction mixture.

No routes to 2-substituted nicotinoids exist in the literature. Because of the substituent pattern involved and the well known resistance of pyridine toward Friedel-Crafts alkylation or acylation, precursors to such compounds are difficult to prepare. In reality, the regiospecific synthesis of polysubstituted pyridines is a continuing problem in modern heterocyclic chemistry.

The approach envisioned by the inventors for preparing 2-alkylnicotinoids involves the addition of an ortho substituent via the rearrangement of a monosubstituted pyridine. Although such reactions have not generally succeeded in pyridine chemistry, [see R. Paul and S. Tchelitcheff, Bull. Soc. Chem. Fr., 2134, (1968)], proper selection of the migrating moiety has made it possible to synthesize the desired 2-alkylnicotinoids. Preliminary results demonstrating the feasibility of these reactions have been published by the inventors in J. Org. Chem., 41, 2658, (1976). The paper describes a new synthetic process for the production of 2-alkyl-3-acylpyridines and 2-alkyl-3-formylpyridines via [2,3]-sigmatropic rearrangement of 1-cyanomethyl-1-[α-alkyl-2-picolyl)-pyrrolidinium salts. The versatility of this procedure is evidenced by the fact that the α-cyanoamine initially obtained can be hydrolyzed to an aldehyde, reductively cleaved to an amine, or alkylated and hydrolyzed to a ketone.

Similar reactions involving homocyclic chemistry have been reported by Mander and Turner in J. Org. Chem., 38, 2915, (1972), wherein the [2,3]-sigmatropic rearrangement of ylids derived from allylic-N-cyanomethylpyrrolidinium salts followed by hydrolysis of the products afforded β, γ,-unsaturated aldehydes.

DESCRIPTION OF THE INVENTION

The present invention concerns new and improved processes for the production of compounds represented by the formula:

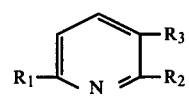

I wherein $R_1$ is a member selected from the group consisting of hydrogen, lower alkyl, arylalkyl or phenylalkyl, $R_2$ is selected from the group consisting of lower alkyl and phenylalkyl, and $R_3$ is selected from the group consisting of heterocyclics represented by the formulae:

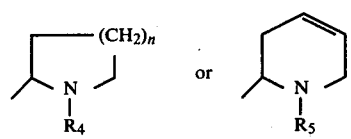

II wherein $R_4$ is selected from the group consisting of hydrogen or lower alkyl, $R_5$ is selected from lower alkyl, and n is one or two.

The present invention additionally relates to intermediate products, some of which are useful in the production of compounds of Formula I and are represented by the formula:

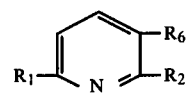

III wherein $R_1$ and $R_2$ are the same as defined in Formula I and $R_6$ is selected from the group represented by the formulae:

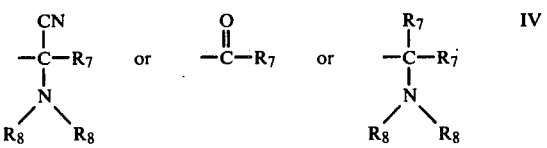

IV wherein $R_7$ is selected from the group consisting of hydrogen, lower alkyl, ω-cyanoalkyl and phenylalkyl, and each $R_8$ is independently selected from lower alkyl or when taken together with a connecting element, a heterocyclic structure is formed. The intermediates are readily prepared by the method dipicted in Scheme II hereinbelow.

As used herein, "lower alkyl" means straight-chain or branched alkyl groups with 1 to 6 carbon atoms, for example methyl, ethyl, propyl, isopropyl, butyl, and the like, with methyl being preferred. "Arylalkyl" means aromatic radicals containing between 6 and 10 carbon atoms such as phenyl, tolyl, xylyl, and the like. "Phenylalkyl" includes radicals such as benzyl, phenylethyl, phenylpropyl, and the like. "Heterocyclic structures" are meant to include cyclic amines such as pyrrolidine, morpholine, pyridine, tetrahydropyridines and the like.

The compounds within the scope of the Formula I have two basic nitrogen atoms and can therefore form acid addition salts with inorganic and organic acids; for example, hydrochloric acid, acetic acid, maleic acid, p-toluenesulfonic acid, ethanesulfonic acid and the like.

The salts of the compounds within the scope of Formula I can also be in the form of hydrates, for example, mono-, tri- or polyhydrate.

DESCRIPTION OF THE PREFERRED EMBODIMENTS

The compounds of Formula I may be synthesized by two different but related processes. In the first and preferred process, a 2-halomethyl or substituted methylpyridine represented by the formula:

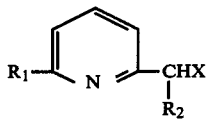

V wherein $R_1$ is the same as defined in Formula I, $R_2$ is hydrogen, lower alkyl, phenyl or phenylalkyl and X is halogen, such as bromide, chloride, iodide or the like, with bromide being preferred, is reacted with a 2-cyano-N-substituted heterocyclic of the formula:

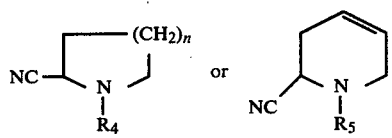

VI wherein $R_4$ and $R_5$ are lower alkyl and n is one or two, to give a 1-alkyl-1-(2-picolyl or 2-α-alkylpicolyl)-2-cyanopyrrolidinium halide or the corresponding 1,2,3,6-tetrahydropyridinium halide.

The 2-haloalkylpyridine starting materials are readily available or may be synthesized by known methods. The 1-alkyl-2-cyanopyrrolidines are prepared by treatment of a 1-alkyl-2-pyrrolidinone with a reducing agent such as sodium aluminum hydride followed by reaction with ammonium cyanide. The 2-cyano-N-substituted-1,2,3,6-tetrahydropyridines are prepared according to methods described in *J. Org. Chem.*, 29, 1647 (1964).

The reaction is carried out by adding a 2-haloalkylpyridine to a 1-alkyl-2-cyanopyrrolidine dissolved in an aprotic polar solvent such as dimethylsulfoxide, acetonitrile, etc. The reaction is allowed to continue until salt formation is complete as determined by, for example, thin layer chromatography.

The [2,3]-rearrangement (Scheme I, below) of the pyrrolidine moiety is achieved by diluting the product (VII) obtained above with an aprotic solvent such as tetrahydrofuran, dimethylsulfoxide, hexamethylphosphoric triamide, acetonitrile, and the like, with tetrahydrofuran being preferred, and then adding a strong nonnucleophilic base such as potassium-tert-butoxide, potassium hydride, sodium hydride, sodium amide, and the like. After an appropriate reaction time of about 4 to about 8 hours, the product is isolated by standard extraction techniques known in the art. Alternatively, the reaction can be carried out using a base such as sodium amide and liquid ammonia as the solvent. The latter method minimizes formation of side products which occur in certain examples. The crude 2-alkyl-2'-cyanonicotine product (VIII) isolated by standard techniques, is then treated with a reducing agent such as lithium aluminium hydride, sodium borohydride, sodium cyanohydride and the like. Heating may be required to complete the reaction and the crude product is then isolated and may be further purified by standard techniques to yield the desired 2-alkylnicotinoids of Formula IX:

Scheme I

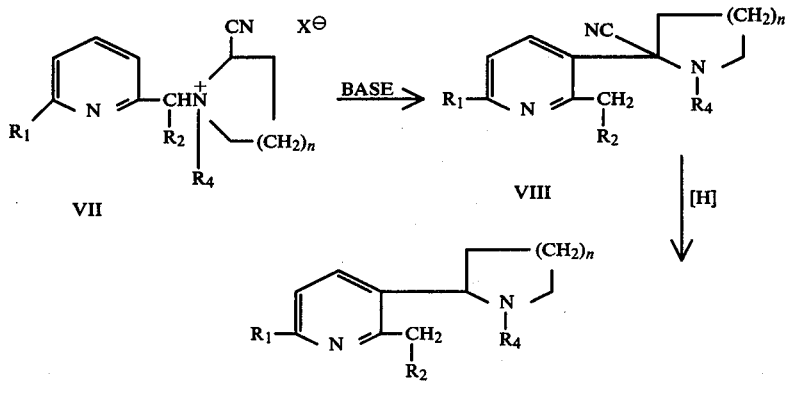

wherein $R_1$ and n are the same as defined in Formulae I and II, $R_2$ is hydrogen, lower alkyl, phenyl, or phenylalkyl and $R_4$ is lower alkyl.

In a similar manner, the [2,3]-rearrangement of the 1-alkyl-1-(2-picolyl or 2-α-alkylpicolyl)-2-cyano-1,2,3,6-tetrahydropyridinium halide is achieved by reaction, preferably with sodium amide in liquid ammonia. Reductive decyanation gives a N'-alkyl-2-substituted-anatabine of Formula X:

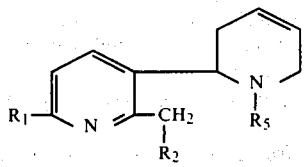

wherein $R_1$ is the same as defined in Formula I, $R_2$ is hydrogen, lower alkyl, phenyl, or phenylalkyl and $R_5$ is lower alkyl. The compound above may be reduced to the corresponding anabasine by known methods.

An alternate process for making the compounds of Formula I is shown in Scheme II below:

Scheme II

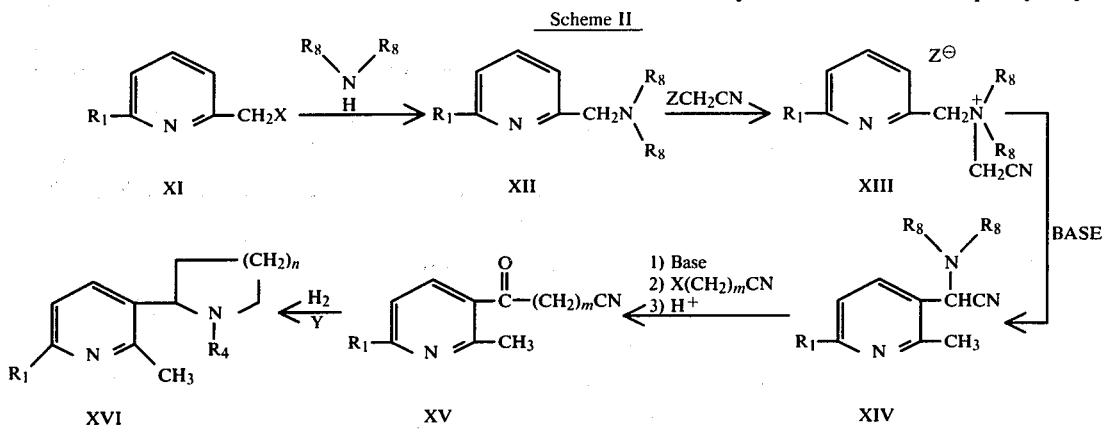

wherein $R_1$ is the same as defined in Formula I, $R_4$ is hydrogen, $R_8$ is the same as defined in Formula IV, X is halogen as defined in Formula V, Y is a catalyst selected from a metal such as platinum or Raney nickel, Z is a group labile to nucleophilic displacement of the group selected from benzenesulfonate, naphthalenesulfonate, tosylate or halogen, and preferably chloride or bromide, m is 2 or 3 and n is the same as defined in Formula II.

Alkylation of a 2-halopicoline with a secondary amine such as pyrrolidine yields 1-(2-picolyl)pyrrolidine (XII). The reaction is generally carried out in an aprotic solvent with gentle heating followed by stirring at room temperature. The isolated and distilled product, 1-(2-picolyl)pyrrolidine is then converted to a crystalline, quaternary salt by reaction with a compound of the formula Z-CH$_2$CN wherein Z is as defined hereinabove, in an aprotic solvent to yield the corresponding salt (XIII). The α-cyanoamine thus formed serves as the migrating moiety in a Sommelet-Hauser rearrangement when treated with an excess of a strong, nonnucleophilic base. The initial rearrangement product, a 2-alkyl-3-(1-cyano-1-pyrrolidinylmethyl)pyridine (XIV) is generally not isolated, but its formation may be confirmed by pmr spectroscopy. The compounds of Formula (XIV) may then be treated with one equivalent of a strong base, followed by alkylation with a haloalkylnitrile, and acid hydrolysis to give a 2-methyl-3 pyridine cyanoalkyl ketone of Formula (XV). The ketone thus formed may be cyclized under reducing conditions to yield compounds of Formula (XVI). The reduction can be carried out catalytically, by means of noble metal catalyst, for example, by means of platinum, or by means of Raney nickel catalyst under elevated pressure, for example, under a pressure of more than 2 atmospheres. The compounds of Formula I obtained in the manner described above are unsubstituted at the nitrogen, i.e. $R_4$ is hydrogen. Alternatively, the α-cyanoamine resulting from the rearrangement may be reduced to the corresponding amine or treated with an organometallic to form an alkylated amine.

It yet another aspect of the present invention, when $R_2$ of Formula I is an alkyl group other than methyl, for example, ethyl or propyl, the compound may be prepared by starting with the appropriate 2-α-alkylpicoline as previously described herein above (Scheme I and Scheme II), or in an alternate approach by further alkylation of $R_2$. For example, 2-methylnicotine may be readily converted to 2-ethylnicotine by treatment with phenyllithium followed by alkylation with a haloalkyl such as methyliodide. In a similar manner, 2-methylnicotine may be converted to a 2-phenylalkylnicotine by treatment with phenyllithium and alkylation with a haloalkylphenyl moiety to yield a compound of Formula I, such as, for example, 2-phenylethylnicotine.

The following examples are illustrative but not limitive of the compounds of this invention and the procedures for their preparation. Temperatures stated are in degrees centigrade and all reactions were run in an inert atmosphere such as nitrogen.

PREPARATION OF STARTING MATERIALS

Preparation I

1-Methyl-2-cyanopyrrolidine

To 20 g of 1-methyl-2-pyrrolidinone in 250 ml of dry tetrahydrofuran was added, over a period of one hour, 26 ml of a 70% solution of sodium bis-(methoxyethoxy)aluminum hydride in benzene at 0° C. The reaction mixture was stirred for an additional hour at 0° C. and then for two hours at room temperature.

A solution of 29.4 g of potassium cyanide in 340 ml of water was added and the resulting mixture was stirred overnight at room temperature. Thereafter it was refluxed for 30 minutes.

The reaction mixture was cooled and the organic and aqueous phases separated. The aqueous phase was washed with 100 ml of ether. The ether and tetrahydrofuran phases were then combined and washed with two 100 ml portions of a saturated sodium chloride solution. The organic phase was dried over sodium sulfate and filtered preparatory to removal of solvent under reduced pressure. The residue was distilled to yield 10.0 g of 1-methyl-2-cyanopyrrolidine. The compound had a boiling point of 57°–9° at 9.5 mm of Hg.

Preparation II

1-Cyanomethyl-1-(2-picolyl)pyrrolidinium benzenesulfonate

To 20.0 g (0.124 mole) of 1-(2-picolyl)pyrrolidine, obtained via the alkylation of 2-bromomethylpyridine with pyrrolidine, in 100 ml acetonitrile was added one equivalent of cyanomethyl benzenesulfonate in 50 ml acetonitrile maintaining the temperature at about 25°. After the addition was complete, the reaction was stirred at room temperature for 18 hours. The acetonitrile was removed under reduced pressure and tetrahydrofuran was added. The crystalline product was collected by filtration and washed with tetrahydrofuran and ether. After air drying, the yield of colorless crystals was 38.5 g (86%), m.p. 118.5°–120°.

Anal. Calcd. for $C_{18}H_{21}N_3O_3S$: C, 60.14; H, 5.89; N, 11.69; S, 8.92 Found: C, 60.40; H, 5.89; N, 11.72; S, 8.82

Spectral data are tabulated below:

| Infrared Spectrum | | |
|---|---|---|
| Group | Wavenumber (cm$^{-1}$) | Intensity |
| ArSO$_3$$^-$ | 1205 | very strong |
| Phenyl | 1595 | medium |
| 3-Substituted pyridine | 1580 | weak |
| Phenyl | 725 | strong |
| 3-Substituted pyridine | 765 | strong |

| NMR Spectrum | | | | |
|---|---|---|---|---|
| Proton | Chem. Shift (δ) | Splitting Pattern | J(Hz) | No. of Protons |
| β-Pyrrolidine-H | 2.17 | m | — | 4 |
| α-Pyrrolidine-H | 3.82 | m | — | 4 |
| Py-CH$_2$-N | 4.82 | s | — | 2 |
| N-CH$_2$-CN | 4.95 | s | — | 2 |
| Aromatic | 6.59 | m | — | 8 |
| Aromatic | 7.59 | m | — | 1 |

Preparation III

2-Methyl-3-pyridyl 2-cyanoethyl ketone

A solution of 12.32 g (34.6 mmol) of 1-cyanomethyl-1-(2-picolyl)pyrrolidinium benzenesulfonate in 125 ml of dry dimethylsulfoxide was prepared and 290 ml of dry tetrahydrofuran was added. The solution was cooled to $-10°$, and 1.84 g (38.1 mmol) of 50% sodium hydride in mineral oil was added. The mixture was stirred at $-5°$ to $-10°$ for 0.5 hour and allowed to warm to room temperature over 1.5 hours. An additional 1.84 g (38.1 mmol) of 50% sodium hydride in mineral oil was added, the mixture was heated under reflux for 0.5 hour, and then cooled to $-10°$. A solution of 5.1 g (38 mmol) of 3-bromopropionitrile in 25 ml tetrahydrofuran was added over a 0.5 hour period and the reaction stirred for an additional 0.5 hour. The reaction mixture was filtered and concentrated under reduced pressure. The residue was dissolved in ether and the ethereal solution was washed three times with a saturated sodium chloride-potassium carbonate solution. The aqueous washes were discarded and the organic phase was filtered and dried over sodium sulfate. Evaporation of the solvent gave 8.17 g of brown oil. To the oil were added 5 ml of tetrahydrofuran, 15 ml water, and 30 ml of acetic acid. The solution was stirred at 53° for 24 hours, the volume reduced to 20 ml under reduced pressure and acidified with 40 ml of 2.2 N HCl. The aqueous solution was washed with two portions of ether, basified with potassium carbonate, and extracted with methylene chloride. The methylene chloride solution was dried over magnesium sulfate and the solvent removed. The residue was distilled (147° at 0.1 mm Hg) to yield a yellow oil which crystallized on trituration with ether. The colorless crystals were collected and dried. The yield of product was 3.2 g (53%), m.p. 82°–83.5°.

Anal. Calcd. for $C_{10}H_{10}N_2O$: C, 68.95, H, 5.79; N, 16.08 Found: C, 69.13; H, 5.80; N, 16.13

Spectral data are tabulated below:

| Infrared Spectrum | | |
|---|---|---|
| Group | Wavenumber (cm$^{-1}$) | Intensity |
| CN | 2220 | medium |
| $\underset{\text{PyC}-}{\overset{O}{\|\|}}$ | 1675 | very strong |
| PyCH$_3$ | 1370 | medium |
| 2,3-Disubstituted pyridine | 770 | medium |

| NMR Spectrum | | | | |
|---|---|---|---|---|
| Proton | Chem. Shift (δ) | Splitting Pattern | J(Hz) | No. of Protons |
| Py—CH$_3$ | 2.73 | s | — | 3 |
| $\overset{O}{\underset{-C-CH_2-CH_2CN}{\|\|}}$ | 2.76 | t | — | 2 |
| $\overset{O}{\underset{-C-CH_2CH_2CN}{\|\|}}$ | 3.32 | t | 8 | 2 |
| 5-PyH | 7.28 | dd | $J_{5,4}=8$ $J_{5,6}=5$ | 1 |
| 4-PyH | 8.00 | dd | $J_{4,6}=2$ $J_{4,5}=8$ | 1 |
| 6-PyH | 8.65 | dd | $J_{6,4}=2$ $J_{6,5}=5$ | 1 |

Preparation IV

1-(1-Pyrrolidinyl)-1-(2-pyridyl)ethane

To 25.0 g (0.134 mol) of 2-(1-pyrrolidinyl)-2-(2-pyridyl)acetonitrile, prepared by the reaction of pyridine-2-carboxaldehyde with potassium cyanide and pyrrolidinium perchlorate, in 75 ml dry dimethylsulfoxide and 200 ml tetrahydrofuran at $-10°$ was added 7.75 g (0.161 mol) of 50% sodium hydride dispersion. After no further gas evolution was observed, a solution of 22.34 g (0.161 mol) of methyl iodide in 10 ml tetrahydrofuran was added over a 10 minute period. After addition had been completed, the reaction mixture was warmed to 40° for two minutes and cooled to 15°. The reaction mixture was filtered and the precipitate was washed with methylene chloride. The filtrates were combined, washed with saturated sodium chloride solution, and dried over sodium sulfate. Removal of the solvent gave 24.75 g (92%) of the crude product, 2-(1-pyrrolidinyl)-2-(2-pyridyl)propionitrile. The total crude product was dissolved in 500 ml 95% ethanol, cooled to 5° and treated with 9.3 g (0.245 mol) sodium borohydride. The reaction mixture was stirred at room temperature for 20 hours and the filtered. Removal of the solvent at reduced pressure gave a tan oil which was dissolved in hexane and dried over sodium sulfate. The hexane solution was then filtered and concentrated. The crude product was distilled (78°–80°/0.2 mm Hg) to give 20.77 g (88%) of 1-(1-pyrrolidinyl)-1-(2-pyridyl)ethane.

Anal. Calcd. for $C_{11}H_{16}N_2$: C, 74.95; H, 9.15; N, 15.90 Found: C, 74.93; H, 9.23; N, 15.81

Spectral data are tabulated below:

| | Infrared Spectrum | |
|---|---|---|
| Group | Wavelength (cm$^{-1}$) | Intensity |
| 2-Substituted pyridine | 1590, 1579, 745 | Strong |
| $CH_3$ | 1365 | Strong |

| | NMR Spectrum | | |
|---|---|---|---|
| Proton | Chem. Shift ($\delta$) | Splitting Pattern | J(Hz) | No. of Protons |
| $CH_3$ | 1.43 | d | 6.5 | 3 |
| 3',4'-H | 1.77 | m | — | 4 |
| 2',5'-H | 2.50 | m | — | 4 |
| $CH_3$—CH | 3.44 | q | 6.5 | 1 |
| 3,4,5-PyH | 7.33 | m | — | 3 |
| 6-PyH | 8.55 | m | — | 1 |

EXAMPLE 1

2-Methylnicotine or
2-Methyl-3-(1-methyl-2-pyrrolidinyl)pyridine

An ethereal solution of 2-bromomethylpyridine, obtained by treating 9.0 g (35.6 mmol) of 2-bromomethylpyridine hydrobromide with aqueous sodium bicarbonate, was added to 4.30 g (39 mmol) of 1-methyl-2-cyanopyrrolidine in 100 ml dimethylsulfoxide. The ether was removed at reduced pressure, and the solution was stirred at room temperature for 24 hrs. To the solution was added 500 ml dry tetrahydrofuran and, after cooling to −20°, 4.0 g (35.8 mmol) of freshly sublimed potassium-t-butoxide was added. The reaction mixture was stirred for 5 hours at −20°, after which the tetrahydrofuran was removed under reduced pressure. A mixture of 50 ml ether and 50 ml ice water was added and the organic phase was separated. The aqueous phase was further extracted, and the combined extracts washed with three 50 ml portions of saturated sodium chloride and 10 ml 50% potassium hydroxide, and then dried over sodium sulfate. Removal of the ether gave 3.74 g of a crude product which was dissolved in 60 ml ether and added to a slurry of 1.41 g (37 mol) of lithium aluminium hydride in 120 ml ether maintained at 0°. The solution was stirred at 0° for 0.5 hour and then heated under reflux for 3 hours. After cooling to 0°, 15 ml of saturated potassium carbonate was added dropwise, and the resulting mixture was heated under reflux for 0.5 hour. The mixture was filtered, and the filtrate was extracted with two 10 ml portions of 20% aqueous acetic acid. The aqueous phase was then adjusted to ~pH 10 with 50% aqueous potassium hydroxide, and the basic solution was extracted with four 25 ml portions of ether. The ether extracts were combined, washed with saturated sodium chloride, and dried over sodium sulfate. After filtration and removal of the ether, the crude product was distilled (56°–59°/0.1 mm) to give 1.22 g (19.5%) of 2-methylnicotine which was a colorless liquid.

Anal. Calcd. for $C_{11}H_{16}N_2$: C, 74.95; H, 9.15; N, 15.90 Found: C, 75.04; H, 9.06; N, 15.68

Spectral data are tubulated below:

| | Infrared Spectrum | |
|---|---|---|
| Group | Wavenumber (cm$^{-1}$) | Intensity |
| 2,3-Disubstituted pyridine | 805, 740 | medium |
| Py-$CH_3$ | 1380 | strong |

| | NMR Spectrum | | | |
|---|---|---|---|---|
| Proton | Chem. Shift ($\delta$) | Splitting Pattern | J(Hz) | No. of Protons |
| Py-$CH_3$ | 2.20 | s | — | 3 |
| N-$CH_3$ | 2.58 | s | — | 3 |
| 2'+5'-cis | 3.32 | m | | 2 |
| 5-PyH | 7.16 | dd | $J_{5,6}=6$ $J_{5,4}=8$ | 1 |
| 4-PyH | 7.87 | dd | $J_{4,5}=8$ $J_{6,5}=1$ | 1 |
| 6-PyH | 8.39 | dd | $J_{6,5}=6$ $J_{6,4}=1$ | 1 |

EXAMPLE 2

2-Methylnornicotine or
2-Methyl-3-(2-pyrrolidinyl)pyridine

To a solution of 3.15 g 2-methyl-3-pyridyl 2-cyanoethyl ketone (Preparation III) in 180 ml of ethanol saturated with ammonia was added 20 g of freshly prepared Raney nickel. The mixture was hydrogenated in a Parr apparatus at about 50 psi for 15 h. The reaction mixture was filtered to remove the catalyst and concentrated under reduced pressure. The residue was taken up in hexane and dried over Drierite. After filtration and removal of the solvent the residue was distilled. The fraction boiling at 100°–105°/0.175 mm Hg, was collected to give 2.1 g (75%) of 2-methylnornicotine.

Anal. Calcd. for $C_{10}H_{14}N_2$: C, 74.03; H, 8.70; N, 17.27 Found: 73.93; H, 8.75; N, 16.99

Spectral data are tabulated below:

| | Infrared Spectrum | |
|---|---|---|
| Group | Wavenumber (cm$^{-1}$) | Intensity |
| NH | 3295 | medium |
| 2,3-Disubstituted pyridine | 1520, 1530, 800 | strong |

| | NMR Spectrum | | | |
|---|---|---|---|---|
| Proton | Chem. Shift ($\delta$) | Splitting Pattern | J(Hz) | No. of Protons |
| 3',4'-H | 1.68 | m | — | 4 |
| Py-$CH_3$ | 2.53 | s | — | 3 |
| 5'-H | 3.10 | m | — | 2 |
| 2'-H | 4.30 | t | 7 | 1 |
| 5-PyH | 7.07 | dd | $J_{5,6}=5$ $J_{5,4}=8$ | 1 |
| 4-PyH | 7.88 | dd | $J_{4,6}=2$ $J_{4,5}=8$ | 1 |
| 6-PyH | 8.35 | dd | $J_{6,4}=2$ $J_{6,5}=5$ | 1 |

EXAMPLE 3

2,6-Dimethylnicotine or
2,6-Dimethyl-3-(1-methyl-2-pyrrolidinyl)pyridine To a solution of 22.09 g (82.7 mmol) 2-bromomethyl-6-methylpyridine hydrobromide in 40 ml water was added 40 ml methylene chloride and 6.95 g (82.7 mmol) sodium bicarbonate at 0°. The methylene chloride portion was separated and the aqueous solution extracted with three 50 ml portions of methylene chloride. The methylene chloride extracts were combined, dried over magnesium sulfate, filtered, and concentrated to 35 ml under reduced pressure. A 50 ml portion of tetrahydrofuran was added and the solution was again concentrated to 35 ml under reduced pressure. A solution of 10 g (91 mmol) of 1-methyl-2-cyanopyrrolidine in 100 ml dimethylsulfoxide was added and the solution was stirred overnight at room temperature. The dimethylsulfoxide was removed under reduced pressure to give a viscous yellow oil.

The resulting oil was dissolved in 100 ml dimethylsulfoxide and 500 ml tetrahydrofuran and then cooled to −10°. To the solution was added 4.5 g (94 mmol) 50% sodium hydride dispersion. The reaction was stirred for 3.5 hours at 0° and 16 hours at room temperature. The reaction mixture was filtered and the solvent was removed under reduced pressure giving a tan oil containing some solid material. The oil was dissolved in a small amount of ether and the solution filtered to remove insolubles. The ether solution was washed three times with a basic saturated sodium chloride solution, dried over sodium sulfate, filtered and concentrated to give 14.96 g of an oil. The oil was dissolved in 300 ml 95% ethanol and 4.7 g (124 mmol) of sodium borohydride was added. The mixture was stirred at 0° for 1 hour and at room temperature for 2 hours. The reaction mixture was filtered and the precipitate was washed first with ethanol and then with ether. The filtrate was concentrated, taken up in ether and filtered to remove additional insolubles. The filtrate was extracted with three 20 ml portions of 20% acetic acid. The combined acid extracts were washed with ether, diluted with 11.3 ml of concentrated hydrochloric acid and concentrated to dryness. The residue was treated with 50% aqueous potassium hydroxide and extracted with three portions of ether. The ether extracts were combined and dried over sodium sulfate. Concentration of the ether solution gave 12.88 g of crude product which was distilled. A 6.2 g fraction boiling from 88°–135°/0.25 mm Hg, was collected which was primarily the desired product with some contaminants present. Chromatography of this fraction on 200 g of basic alumina, activity grade I, with 2% ethyl acetate in hexane gave about 4.6 g of product. Distillation (63°–64°/0.05 mm Hg) yielded 3.8 g (25%) of pure 2,6-dimethylnicotine.

Anal. Calcd. for $C_{12}H_{18}N_2$: C, 75.74; H, 9.54; N, Found: C, 75.61; H, 9.62; N, 14.64

Spectral data are tabulated below:

| Group | Infrared Spectrum Wavenumber (cm$^{-1}$) | Intensity |
|---|---|---|
| 2,3,6-Trisubstituted pyridine | 1590, 1515, 825 | medium |
| —CH$_3$ | 1350 | strong |

| Proton | NMR Spectrum Chem. Shift (δ) | Splitting Pattern | J(Hz) | No. of Protons |
|---|---|---|---|---|
| 3′,4′,cis-5′-H | 1.8 | m | — | 5 |
| N—CH$_3$ | 2.15 | s | — | 3 |
| PyCH$_3$ | 2.48 | s | — | 3 |
| PyCH$_3$ | 2.51 | s | — | 3 |
| 2′, trans-5′-H | 3.28 | t | 8 | 2 |
| 5-PyH | 6.99 | d | 9 | 1 |
| 4-PyH | 7.81 | d | 9 | 1 |

EXAMPLE 4

2-Methylanabasine or 2-Methyl-3-(2-piperidinyl)pyridine

The preparation of 2-methyl-3-pyridyl-3-cyanopropyl ketone was carried out using the procedure described for the synthesis of 2-methyl-3-pyridyl 2-cyanomethyl ketone (Preparation III) except that 4-bromobutyronitrile was used instead of 3 bromopiopionitrile. A solution of 2.8 g of the ketone in 150 ml ammonia saturated ethanol was prepared and 10 g of freshly prepared Raney nickel was added. The mixture was hydrogenated for 20 hours in a Parr apparatus at 67 psi. The reaction mixture was worked up as in Example 2. The product was isolated by distillation (108°–112°/0.2 mm Hg) to give 2.2 g (89%) of 2-methylanabasine.

Anal. Calcd. for $C_{11}H_{16}N_2$: C, 74.95; H, 9.15; N, 15.90 Found: C, 75.04; H, 8.96; N, 15.81

Spectral data are tabulated below:

| Group | Infrared Spectrum Wavelength (cm$^{-1}$) | Intensity |
|---|---|---|
| NH | 3290 | weak |
| 2,3-Disubstituted pyridine | 1570, 795 | strong |
| —CH$_3$ | 1350 | strong |

| Proton | NMR Spectrum Chem. Shift (δ) | Splitting Pattern | J(Hz) | No. of Protons |
|---|---|---|---|---|
| Piperidine + NH | 1.74 | m | — | 5 |
| | 2.38 | m | — | 3 |
| | 3.79 | m | — | 2 |
| PyCH$_3$ | 2.54 | s | — | 3 |
| 5-PyH | 7.08 | dd | $J_{5,4} = 8$ $J_{5,6} = 5$ | 1 |
| 4-PyH | 7.47 | dd | $J_{4,6} = 2$ $J_{4,5} = 8$ | 1 |
| 6-PyH | 8.43 | dd | $J_{6,4} = 2$ $J_{6,5} = 5$ | 1 |

EXAMPLE 5

2-Ethylnornicotine or 2-Ethyl-3-(2-pyrrolidinyl)pyridine

To 5.0 g (28.4 mmol) of 1-(1-pyrrolidinyl)-1-(2-pyridyl)ethane (Preparation IV) in 30 ml acetonitrile was added 5.6 g (28.4 mmol) of cyanomethyl benzenesulfonate. After standing three days the reaction mixture was concentrated on a rotary evaporator and then subjected to continuous ether extraction. The crude product was dried and transferred to a 500 ml three-necked flask to which about 250 ml anhydrous ammonia was added. The resulting solution was stirred at −35° and 1.45 g (37.2 mmol) of sodium amide was added. The reaction mixture was stirred for four hours at −35° and then allowed to warm to room temperature and stand overnight. Ether was added to the residue, and the resulting solution was washed with a saturated sodium chloride solution and dried over sodium sulfate. Removal of the solvent gave 4.88 g of a tan oil. The oil was dissolved in 70 ml dimethylsulfoxide and 300 ml tetrahydrofuran to which 1.48 g (30.8 mmol) of 50% sodium hydride dispersion was added. The mixture was heated under reflux for 30 minutes and then cooled to −10°. A solution of 1.48 g (30.8 mmol) of 3-bromopropionitrile in 10 ml tetrahydrofuran was added over a 15-minute period, the cooling bath was removed, and the reaction mixture was stirred for 1 hour. The mixture was filtered and the solvent was removed, first on the rotary evaporator and then under high vacuum. The residue was dissolved in ether, and the ethereal solution was washed with two portions of 50% potassium hydroxide soluton and one portion of saturated sodium chloride. The ether solution was dried over sodium sulfate and then concentrated to give 3.78 g of tan oil. The oil was dissolved in 5 ml tetrahydrofuran, 15 ml water and 30 ml glacial acetic acid. The solution was maintained at 53° overnight, after which most of the solvent was removed on the rotary evaporator. Ether was added to the residue, and the ethereal solution was extracted with three 5 ml portions of 5% hydrochloric acid. The acid washes were combined and basified with potassium carbonate. The basic solution was extracted with methylene chloride. The methylene chloride extracts were combined and dried over sodium sulfate. Solvent was removed and the residue was distilled (150°-5°/0.05 mm Hg) to give 1 g of a yellow oil. A 500 mg sample of the crude product was dissolved in 100 ml absolute ethanol and the compound was hydrogenated at about 60 psi for 20 hours. The product was worked up as in Example 2, and purification was effected by preparative thin layer chromatography yielding 125 mg of a light yellow oil.

Anal. Calcd. for $C_{11}H_{16}N_2$: C, 74.95; H, 9.15; N, 15.90 Found: C, 75.07; H, 9.25; N, 16.01

Spectral data are tabulated below:

| Infrared Spectrum | | |
|---|---|---|
| Group | Wavelength (cm$^{-1}$) | Intensity |
| —NH | 3300 | medium |
| 2,3-Disubstituted pyridine | 1585, 1575, 800 | strong |
| $CH_3$ | 1305 | strong |

| NMR Spectrum | | | | |
|---|---|---|---|---|
| Proton | Chem. Shift ($\delta$) | Splitting Pattern | J(Hz) | No. of Protons |
| $CH_2$—$CH_3$ | 1.30 | t | 8 | 3 |
| 3',4',N—H | 1.94 | m | — | 5 |
| $CH_2$—$CH_3$ | 2.88 | q | 8 | 2 |
| 5'-H | 3.08 | m | — | 2 |
| 2'-H | 4.37 | t | 7 | 1 |
| 5-PyH | 7.10 | dd | $J_{5,4}=6$ $J_{5,6}=5$ | 1 |
| 4-PyH | 7.88 | dd | $J_{4,5}=6$ $J_{4,6}=2$ | 1 |
| 6-PyH | 8.12 | dd | $J_{6,5}=5$ $J_{6,4}=2$ | 1 |

EXAMPLE 6

2-Ethylnicotine or 2-Ethyl-3-(1-methyl-2-pyrrolidinyl)pyridine

To 176 mg (1 mmol) of 2-methylnicotine in 15 ml anhydrous ether was added 1.1 ml of 1.05 M phenyllithium solution. The reaction mixture was refluxed for 2.5 h after which it was cooled to $-10°$ and 75 $\mu$l (1.2 mmol) methyl iodide was added. The solution was stirred overnight at room temperature. A few drops of methanol were added, the solution was filtered and the solvent was removed. The residue was dissolved in hexane, filtered once again, and the hexane was removed to give 70 mg of crude product. A gas chromatograph of the crude product showed a single major peak. Samples for elemental analysis and spectral data were obtained by preparative gas chromotography.

Anal. Calcd. for $C_{12}H_{18}N_2$: C, 75.74; H, 9.54; N, 14.72 Found: C, 75.74; H, 9.70; N, 14.66

Spectral data are tabulated below:

| Infrared Spectrum | | |
|---|---|---|
| Group | Wavelength (cm$^{-1}$) | Intensity |
| 2,3-Disubstituted pyridine | 1570, 800 | strong |
| —N—$CH_3$ | 1385 | strong |

| NMR Spectrum | | | | |
|---|---|---|---|---|
| Proton | Chem. Shift ($\delta$) | Splitting Pattern | J(Hz) | No. of Protons |
| $CH_2CH_3$ | 1.31 | t | 8 | 3 |
| —N—$CH_3$ | 2.30 | s | — | 3 |
| $CH_2$—$CH_3$ | 2.84 | t | 8 | 2 |

EXAMPLE 7

N',2-dimethylanatabine or 2-Methyl-3-[1-methyl-2-(1,2,3,6-tetrahydropyridinyl)-]pyridine To a solution of 8.09 g (31.9 mmol) of 2-bromomethylpyridine hydrobromide in 15 ml water was added 25 ml methylene chloride. The mixture was cooled to 0° and a slight excess of sodium bicarbonate was added. The organic phase was separated and the aqueous phase was extracted with an additional 25 ml of methylene chloride. The organic phases were combined, extracted with two portions of saturated brine, dried over magnesium sulfate and filtered. To the filtered solution was added 3.89 g (31.9 mmol) of 1,2,3,6-tetrahydro-1-methyl-2-cyanopyridine and 50 ml tetrahydrofuran. The solution was concentrated to about 15 ml after which 30 ml dimethyl sulfoxide was added, and the reaction mixture was stirred for 21 hours. The solution was continuously extracted with ether and the ether insoluble residue was dissolved in methanol, transferred to a 500 ml three-necked flask, and evaporated in vacuo to dryness to give 7.33 g (79%) of a dark red semi-solid. Two hundred fifty ml of liquid ammonia was condensed into the flask and 1.23 g (31.4 mmol) of sodium amide was added. The reaction mixture was stirred at $-60°$ for 30 minutes and then at reflux for 2 hours. The ammonia was allowed to boil off leaving a brown residue which was triturated with ether and the resulting ether solution was filtered, and concentrated to give 2.71 g of a brown oil. The oil was dissolved in 125 ml of 95% ethanol and 2.0 g of sodium borohydride was added. After stirring at room temperature for 8 hours, the ethanol was removed and the residue was dissolved in ether. The etheral solution was extracted with 5% hydrochloric acid, the acid solution was washed with ether, basified with aqueous potassium hydroxide, and extracted with ether. The ether extracts of the basic solution were combined, dried over magnesium sulfate, filtered, and the solvent was removed. The residue was distilled, and the fraction boiling at 95°-100°/0.1 mm Hg was collected to give 800 mg of a yellow liquid which was primarily N',2-dimethylanatabine (80%). The impurity was not identified, but spectral data indicate that it too is a 2,3-disubstituted pyridine. Spectral data and elemental analyses were obtained from samples collected by preparative glc.

Anal. Calcd. for $C_{12}H_{16}N_2$: C, 76.55; H, 8.57; N, 14.88 Found: C, 76.40; H, 8.65; N, 14.82

Spectral data are tabulated below:

| Infrared Spectrum | | |
|---|---|---|
| Group | Wavelength (cm$^{-1}$) | Intensity |
| 2,3-Disubstituted pyridine | 1585, 1575, 805 | medium |
| Double bond | 1670 | weak |

| NMR Spectrum | | | | |
|---|---|---|---|---|
| Proton | Chem. Shift ($\delta$) | Splitting Pattern | J(Hz) | No. of Protons |
| N—$CH_3$ | 2.09 | s | — | 3 |
| 3+-H | 2.27 | m | — | 2 |
| Py—$CH_3$ | 2.62 | s | — | 3 |
| cis-6'-H | 2.98 | m | — | 1 |
| 2', trans-6'-H | 3.48 | m | — | 2 |

| | | | | |
|---|---|---|---|---|
| 4',5'-H | 5.81 | s | — | 2 |
| 5-PyH | 7.18 | dd | $J_{5,4} = 8$<br>$J_{5,6} = 4$ | 1 |
| 4-PyH | 7.79 | dd | $J_{4,5} = 8$<br>$J_{4,6} = 1$ | 1 |
| 6-PyH | 8.41 | dd | $J_{6,5} = 1$<br>$J_{6,4} = 1$ | |

EXAMPLE 8

2-Methyl-6-phenylnicotine 2-methyl-6-phenylpyridine, obtainable from 1,3-pentadiene and benzonitirle via the procedure of Janz and McColloch [*J. Am. Chem. Soc.*, 77 (1955), 3413] is treated with N-bromosuccinimide to give 2-bromomethyl-6-phenylpyridine. The bromomethyl compound is treated with 1-methyl-2-cyanopyrrolidine, and the resulting salt is rearranged using sodium amide in liquid ammonia and decyanated with sodium borohydride in ethanol according to the procedures described in Example 1. The product can be purified by distillation.

EXAMPLE 9

2-(2-Phenylethyl)nicotine 2-methylnicotine is treated with phenyllithium as in Example 6. To the resulting anion is added a slight excess of benzyl bromide. The product can be isolated by distillation.

EXAMPLE 10

2,6-Dimethyl-3-(1-dimethylamino-2-phenylethyl)pyridine 2-bromomethyl-6-methylpyridine is treated with dimethylamine to give the corresponding tertiary amine, 2-dimethylaminomethyl-6-methylpyridine. The tertiary amine is treated with cyanomethyl benzenesulfonate, as in Preparation II, to give dimethylcyanomethyl-(6-methyl-2-picolyl) ammonium benzene sulfonate. The quaternary ammonium salt is rearranged using sodium hydride and alkylated with benzylbromide according to the procedure described in Example 2. The alkylated cyanoamine is decyanated with sodium borohydride in ethanol to give the desired product which can be purified through its picrate.

EXAMPLE 11

2-Methyl 3-(1-N-pyrrolidinyl-3-cyanopropyl)pyridine 1-cyanomethyl-1-(2-picolyl)pyrrolidinium benzenesulfonate (see Preparation II) is rearranged and alkylated with 3-bromopropionitrile as in Example 2. The resulting dicyanoamine is decyanated with sodium borohydride in ethanol to give the product. Purification is effected via the picrate.

EXAMPLE 12

A 100 mg sample of the candidate compound was dissolved in 10 ml absolute ethanol. To the solution was added 40 ml tap water containing 0.5 ml of 1% surfactant. A 5 ml sample of each solution was sprayed on to replicate ivy cuttings infested with Aphids. The results, tabulated below in Table I were recorded 18 hours following the application of the sprays.

Table 1

| Compound | Replicate No. | No. of Aphids Alive | Dead | % Dead | Avg. % Dead |
|---|---|---|---|---|---|
| 2-methylnicotine | 1 | 54 | 2 | 4 | |
| | 2 | 38 | 2 | 5 | |
| | 3 | 55 | 5 | 8 | 6 |
| 2-methylnornicotine | 1 | 39 | 2 | 2 | |
| | 2 | 27 | 2 | 7 | |
| | 3 | 30 | 0 | 0 | 3 |
| 2,6-dimethylnicotine | 1 | 32 | 0 | 0 | |
| | 2 | 20 | 3 | 13 | |
| | 3 | 87 | 66 | 4 | 6 |
| 2-methylanabasine | 1 | 24 | 39 | 62 | |
| | 2 | 27 | 27 | 50 | |
| | 3 | 87 | 66 | 43 | 52 |
| l-nicotine | 1 | 0 | 45 | 100 | |
| | 2 | 0 | 27 | 100 | |
| | 3 | 0 | 39 | 100 | 100 |

Most of the compounds exhibited less toxicity to aphids than l-nicotine. However, all compounds exhibited a significantly lower mammalian toxicity than l-nicotine. Aphid toxicity and mammalian toxicity can be taken into account simultaneously by examining the ratio of insecticidal toxicity to mammalian toxicity.

Relevant data are shown in Table II below. In the first column, the $LD_{50}$ of the compounds in mice is a measure of their mammalian toxicity. The second column illustrates the effectiveness of the candidate compounds as insecticides as compared to nicotine, whereas the third column is the ratio of insecticidal effectiveness to mammalian toxicity. This ratio shows that the alkylated nicotines are more effective insecticides than nicotine in that they are considerably safer with regard to mammalian response.

Table II

| Compound | $LD_{50}$ (mouse) | Insecticidial Effectiveness | Net Insecticiday Activity* |
|---|---|---|---|
| Nicotine | 0.26 mg/kg | 100% | 1 |
| 2-Methylnor-nicotine | 100 mg/kg | 3% | 11.5 |
| 2,6-Dimethyl-nicotine | 41 mg/kg | 6% | 10 |
| 2-Methylana-basine | 15.7 mg/kg | 52% | 32 |

*This is defined as insecticidal/effectivenesss and is a measure of insecticidal toxicity vs. mammalian toxicity. $\frac{LD_{50} \text{ nicotine}}{LD_{50} \text{ test compound}}$

EXAMPLE 13

A 50 mg sample of the candidate compound was dissolved on 0.4 ml absolute ethanol. A 0.3 μl sample of the solution was applied to the notum of female house flies which has been anesthetized with ether. Results were read twenty-four hours later.

| Compound | Percent Dead in Replicate Run 1 | Run 2 | Avg. % Dead |
|---|---|---|---|
| Nicotine | 100 | 100 | 100 |
| 2-Methylnicotine | 100 | 100 | 100 |
| 2-Methylnornicotine | 80 | 60 | 70 |
| Solvent Control | 0 | 0 | 0 |

The above results demonstrate that with regard to common houseflies, 2-methylnicotine is as effective an insecticide as nicotine itself, while 2-methylnornicotine is only slightly less effective. It is to be noted that previous results demonstrated that 2-methylnicotine possessed lower mammalian toxicity than nicotine.

What is claimed is:

1. A compound represented by the formula:

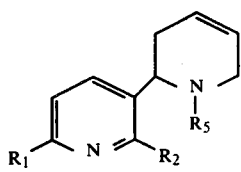

wherein $R_1$ is hydrogen, lower alkyl, phenylalkyl or aralkyl: $R_2$ is lower alkyl or phenylalkyl; and $R_5$ is lower alkyl.

2. The compound 2-methyl-3-(2-pyrrolidinyl) pyridine.

3. The compound 2,6-dimethyl-3-(1-methyl-2-pyrrolidinyl) pyridine.

4. The compound 2-methyl-3-(2-piperidinyl) pyridine.

5. The compound 2-ethyl-3-(2-pyrrolidinyl) pyridine.

6. A compound of claim 1 which is 2-methyl-3-[1-methyl-2-(1,2,3,6-tetrahydropyridinyl)]pyridine.

* * * * *

UNITED STATES PATENT AND TRADEMARK OFFICE
CERTIFICATE OF CORRECTION

PATENT NO. : 4,155,909
DATED : May 22, 1979
INVENTOR(S) : Edward B. Sanders, Henry V. Secor and Jeffrey I. Seeman It is certified that error appears in the above—identified patent and that said Letters Patent is hereby corrected as shown below:

The compound identified at column 15, line 15, should be benzonitrile.

In Example 10, at column 15, lines 45-46, rearrangement in alkylation of the quaternary ammonium salt should be stated to have been accomplished according to the procedure described in Preparation III.

Similarily, in Example 11 at column 15, line 56, the rearrangement and alkylation of 1-cyanomethyl-1-(2-picolyl) pyrrolidinum benzenesulfonate should be stated to have been accomplished as in Preparation III.

The nicotine compound identified in Table I at column 16, line 15, should be $\ell$-nicotine.

Signed and Sealed this

*Thirty-first* Day of *March 1981*

[SEAL]

*Attest:*

RENE D. TEGTMEYER

*Attesting Officer*   *Acting Commissioner of Patents and Trademarks*